(12) United States Patent
Avouris et al.

(10) Patent No.: US 9,594,018 B2
(45) Date of Patent: Mar. 14, 2017

(54) CHEMICAL SENSORS BASED ON PLASMON RESONANCE IN GRAPHENE

(71) Applicant: International Business Machines Corporation, Armonk, NY (US)

(72) Inventors: Phaedon Avouris, Yorktown Heights, NY (US); Damon B. Farmer, White Plains, NY (US); Yilei Li, New York, NY (US); Hugen Yan, Ossining, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/225,286

(22) Filed: Aug. 1, 2016

(65) Prior Publication Data

US 2016/0341661 A1    Nov. 24, 2016

Related U.S. Application Data

(62) Division of application No. 14/313,456, filed on Jun. 24, 2014, now Pat. No. 9,423,345.

(51) Int. Cl.
*G01N 21/75*    (2006.01)
*G01N 21/552*   (2014.01)
*H01L 21/02*    (2006.01)
*H01L 21/311*   (2006.01)
(Continued)

(52) U.S. Cl.
CPC ....... *G01N 21/554* (2013.01); *H01L 21/0277* (2013.01); *H01L 21/02422* (2013.01); *H01L 21/02527* (2013.01); *H01L 21/041* (2013.01); *H01L 21/042* (2013.01); *H01L 21/31144* (2013.01)

(58) Field of Classification Search
CPC .................................................. G01N 21/554
See application file for complete search history.

(56) References Cited

U.S. PATENT DOCUMENTS 4,844,613 A    7/1989   Batchelder et al.
4,889,427 A    12/1989  Van Veen et al.
(Continued)

FOREIGN PATENT DOCUMENTS

EP     0863395 B1       6/2005
WO     WO2010122776 A1  10/2010
WO     WO2011142118 A1  11/2011

OTHER PUBLICATIONS

J. Homola et al., "Surface Plasmon Resonance Sensors: Review," Sensors and Actuators B: Chemical 54, 3 (Jan. 1999).
(Continued)

*Primary Examiner* — Jyoti Nagpaul
(74) *Attorney, Agent, or Firm* — Vazken Alexanian; Michael J. Chang, LLC

(57) ABSTRACT

Techniques for forming nanoribbon or bulk graphene-based SPR sensors are provided. In one aspect, a method of forming a graphene-based SPR sensor is provided which includes the steps of: depositing graphene onto a substrate, wherein the substrate comprises a dielectric layer on a conductive layer, and wherein the graphene is deposited onto the dielectric layer; and patterning the graphene into multiple, evenly spaced graphene strips, wherein each of the graphene strips has a width of from about 50 nanometers to about 5 micrometers, and ranges therebetween, and wherein the graphene strips are separated from one another by a distance of from about 5 nanometers to about 50 micrometers, and ranges therebetween. Alternatively, bulk graphene may be employed and the dielectric layer is used to form periodic regions of differing permittivity. A testing apparatus and method of analyzing a sample using the present SPR sensors are also provided.

20 Claims, 7 Drawing Sheets

(51) Int. Cl.
    *H01L 21/027* (2006.01)
    *H01L 21/04* (2006.01)

(56) References Cited

U.S. PATENT DOCUMENTS

| | | | |
|---|---|---|---|
| 4,997,278 | A | 3/1991 | Finlan et al. |
| 5,917,608 | A | 6/1999 | Naya et al. |
| 7,368,009 | B2 | 5/2008 | Okada et al. |
| 7,692,795 | B2 | 4/2010 | Sasaki et al. |
| 8,024,279 | B2 | 9/2011 | Ryhanen et al. |
| 8,363,223 | B2 | 1/2013 | Ran et al. |
| 2012/0028247 | A1 | 2/2012 | Tamura et al. |
| 2012/0134880 | A1 | 5/2012 | Kurkina et al. |
| 2013/0010300 | A1 | 1/2013 | Tamura et al. |
| 2013/0029430 | A1 | 1/2013 | Tamura et al. |

OTHER PUBLICATIONS

J. Homola, "Surface Plasmon Resonance Sensors for Detection of Chemical and Biological Species", Chemical Reviews 108, 462 (2008).

Mattevi et al., "A review of chemical vapour deposition of graphene on copper," J. Mater. Chem., 2011, 21, 3324-3334 (first published Nov. 2010).

Ko et al., "Simple method to transfer graphene from metallic catalytic substrates to flexible surfaces without chemical etching," Journal of Physics: Conference Series, vol. 433, Issue 1 (Apr. 2013) 012002.

Farmer et al., "Behavior of a Chemically Doped Graphene Junction," Applied Physics Letters 94, 213106 (May 2009).

K.V. Sreekanth et al., "Excitation of surface electromagnetic waves in a graphene-based Bragg grating," Scientific Reports, vol. 2, No. 737 (Oct. 2012).

L. Wu et al., "Highly sensitive graphene biosensors based on surface plasmon resonance," Optics Express, vol. 18, No. 14, pp. 14395-14400 (Jun. 2010).

L. Ju et al., "Graphene plasmonics for tunable terahertz metamaterials," Nature Nanotechnology, vol. 6, No. 10, pp. 630-634 (Oct. 2011).

W. Gao et al., "Excitation of Plasmonic Waves in Graphene by Guided-Mode Resonances," ACS Nano, vol. 6, No. 9, pp. 7806-7813 (Aug. 2012).

List of IBM Patents or Applications Treated as Related.

CHEMICAL SENSORS BASED ON PLASMON RESONANCE IN GRAPHENE

CROSS-REFERENCE TO RELATED APPLICATIONS

This application is a divisional of U.S. application Ser. No. 14/313,456 filed on Jun. 24, 2014, the contents of which are incorporated by reference herein.

FIELD OF THE INVENTION

The present invention relates to surface plasmon resonance (SPR) sensors, and more particularly, to techniques for forming nanoribbon or bulk graphene-based SPR sensors and use thereof for analyzing chemical and biological samples.

BACKGROUND OF THE INVENTION

Surface plasmon resonance (SPR) sensing has been demonstrated to be an exceedingly powerful and quantitative probe of the interactions of a variety of chemical and biological processes. SPR sensing provides a means not only for identifying chemical and biological interactions and quantifying their kinetic and energetic properties, but also for employing these interactions as very sensitive chemical and biological detectors. Conventional SPR sensing is performed using plasmons generated at a metal/dielectric interface, with the metal commonly being gold. See, for example, J. Homola et al., "Surface Plasmon Resonance Sensors: Review," Sensors and Actuators B: Chemical 54, 3 (January 1999).

Conventional metal-based plasmonic materials, however, have certain notable limitations. They are designed to operate at predetermined resonance frequencies, which cannot be substantially tuned. Furthermore, the use of metals requires three dimensional design of plasmon-generating structures, and the plasmon field confinement and propagation length are determined by the metal conductivity. It is in these ways that conventional metal-based plasmonic materials are limited.

Thus, improved plasmonic materials for SPR sensing would be desirable.

SUMMARY OF THE INVENTION

The present invention provides techniques for forming nanoribbon or bulk graphene-based surface plasmon resonance (SPR) sensors and use thereof for analyzing chemical and biological samples. In one aspect of the invention, a method of forming a graphene-based SPR sensor is provided which includes the steps of: depositing graphene onto a substrate, wherein the substrate comprises a dielectric layer on a conductive layer, and wherein the graphene is deposited onto the dielectric layer; and patterning the graphene into multiple, evenly spaced graphene strips, wherein each of the graphene strips has a width of from about 50 nanometers to about 5 micrometers, and ranges therebetween, and wherein the graphene strips are separated from one another by a distance of from about 5 nanometers to about 50 micrometers, and ranges therebetween.

In another aspect of the invention, another method of forming a graphene-based SPR sensor is provided which includes the steps of: depositing a dielectric layer on a conductive layer; patterning trenches at regular intervals in the dielectric layer to transform the dielectric layer into a corrugated surface having a series of grooves and ridges, wherein the grooves are formed by the trenches and the ridges are formed by the dielectric layer remaining between the trenches; and depositing bulk graphene onto the corrugate surface of the dielectric layer, wherein the corrugated surface of the dielectric layer provides periodic regions of differing permittivity beneath the bulk graphene including i) first regions having a first permittivity to light and ii) second regions having a second permittivity to light.

In a further aspect of the invention, a testing apparatus is provided. The testing apparatus includes a graphene-based SPR sensor having a conductive layer, a dielectric layer on the conductive layer, and graphene on a side of the dielectric layer opposite the conductive layer; a light source adjacent to a first side of the graphene-based SPR sensor proximal to the graphene; and a detector adjacent to a second side of the graphene-based SPR sensor proximal to the conductive layer. The graphene may include multiple, evenly spaced graphene strips, wherein each of the graphene strips has a width of from about 50 nanometers to about 5 micrometers, and ranges therebetween, and wherein the graphene strips are separated from one another by a distance of from about 5 nanometers to about 50 micrometers, and ranges therebetween. The dielectric layer may have trenches patterned at regular intervals therein such that the dielectric layer includes a corrugated surface having a series of grooves and ridges, wherein the grooves are formed by the trenches and the ridges are formed by the dielectric layer remaining between the trenches, and wherein the corrugated surface of the dielectric layer provides periodic regions of differing permittivity beneath the bulk graphene including i) first regions having a first permittivity to light and ii) second regions having a second permittivity to light.

In yet another aspect of the invention, a method of analyzing a sample using a graphene-based SPR sensor is provided which includes the steps of: depositing the sample on the graphene-based SPR sensor, wherein the graphene-based SPR sensor includes a conductive layer, a dielectric layer on the conductive layer, and graphene on a side of the dielectric layer opposite the conductive layer, and wherein the sample is deposited onto the graphene; passing light through the sample and the graphene-based SPR sensor, wherein the light induces a plasmon resonance in the graphene, and wherein, by way of an interaction between the plasmon resonance in the graphene and vibrational dipole moments in the sample, an intensity of the light is changed as it passes through the graphene-based SPR sensor; and detecting the intensity of the light that has passed through the sample and the graphene-based SPR sensor, wherein the intensity of light detected represents molecular properties of the sample.

A more complete understanding of the present invention, as well as further features and advantages of the present invention, will be obtained by reference to the following detailed description and drawings.

DETAILED DESCRIPTION OF PREFERRED EMBODIMENTS

Provided herein are graphene-based plasmonic materials and chemical sensors based on plasmon resonance in graphene (i.e., wherein graphene is the surface plasmon active material in the sensor). Graphene plasmon active materials do not suffer from the above-described drawbacks commonly encountered with conventional metal-based plasmonic materials such as gold and silver.

For instance, several factors make graphene a unique platform for plasmon-enhanced infrared spectroscopy: 1) graphene has a two-dimensional lattice structure which allows for a very high plasmon confinement field that cannot be achieved with metal-based plasmons, which promises high sensitivity; 2) the charge concentration of graphene (i.e., the number of majority carriers per unit volume) can be modulated through chemical doping or the field-effect (wherein tuning in this manner is not possible with metal plasmonic structures); 3) the charge concentration profile can be patterned in graphene using standard techniques; and 4) the excitation and coupling to surface plasmons in the resulting structure can be easily achieved. The high carrier mobility and conductivity that are facilitated by the lattice structure of graphene allows for high plasmon field confinement and large plasmon propagation lengths as compared to more conventional gold surfaces of similar thickness. Also, modulation of the charge concentration allows for tuning of surface plasmon energies in graphene, something that cannot be achieved in gold or any other metal. Furthermore, plasmon resonances in graphene can be generated and coupled directly to light by physical confinement of the charge oscillations or by attaching graphene to a dielectric grating. Physical confinement can be achieved by routine oxygen plasma etching, and dielectric grating substrates can be engineered using conventional complementary metal-oxide semiconductor (CMOS) fabrication techniques. See below. Lastly, the plasmon resonance frequency of graphene is in the infrared regime, where most chemicals have their characteristic vibration signals. This makes graphene a natural fit for chemical sensing applications. Thus, it is clear that surface plasmon generation from graphene has characteristics that other plasmon-generating systems lack.

The present techniques are now described in detail by way of reference to FIGS. 1-20. Specifically, an exemplary process for forming graphene-based surface plasmon resonance (SPR) sensors using graphene nanoribbons is provided in FIGS. 1-5. Alternative exemplary processes for forming SPR sensors using bulk graphene are provided in FIGS. 6-11 (employing a corrugated surface) and FIGS. 12-16 (employing a planar surface with periodic regions of different permittivity). Methods of using the present graphene-based SPR sensors for analyzing a sample are then provided in FIGS. 17-18, and 20.

Figure 1:
FIG. 1 is a cross-sectional diagram illustrating a starting structure for forming a graphene-based surface plasmon resonance (SPR) sensor using graphene nanoribbons, the structure including a graphene layer on a side of a dielectric layer opposite a conductive layer according to an embodiment of the present invention.
Figure 2:
FIG. 2 is a cross-sectional diagram illustrating an etch mask having been patterned on the graphene layer according to an embodiment of the present invention.

Referring to FIGS. 1-5, a first exemplary method for forming the present graphene-based SPR sensors is provided. In this example, the graphene is patterned as nanoribbons. As shown in FIG. 1, the process begins with a layer of graphene 102 being deposited on a substrate 104. The substrate 104 preferably includes a (electrically) conductive layer 104a (which will serve as a back gate of the sensor—see below) and an insulating dielectric layer 104b, such that the insulating dielectric layer 104b is deposited on the conductive layer 104a, and the graphene 102 is deposited on a side of the insulating dielectric layer 104b opposite the conductive layer 104a. See FIG. 1.

A suitable (electrically conductive) material for forming conductive layer 104a includes, but is not limited to, intrinsic silicon. Embodiments of the present techniques involve analyzing a sample by passing light through the sample and the sensor (a transmission measurement). In that case, intrinsic silicon is ideal since it is transparent in the correct spectral range and can also be used as an electrostatic gate electrode. Alternatively, conventional gate metals might be employed. For example, one or more of tantalum, titanium, platinum and/or tungsten may be used in forming the conductive layer 104a. However, since these gate metals are not transparent to light, configurations of the present sensors employing a metal back gate would need to be read via a reflection measurement. Any insulating dielectric would be a suitable material for forming insulating dielectric layer 104b. Examples include, but are not limited to, gate dielectrics such as silicon dioxide and aluminum oxide, and high-κ dielectrics such as hafnium oxide or lanthanum oxide.

According to an exemplary embodiment, the insulating dielectric layer 104b has a thickness $T_{Dielectric1}$ of from about 1 nanometer (nm) to about 5 nm, and ranges therebetween. See FIG. 1. By contrast, in the bulk graphene-based fabrication process flows presented below, a thicker starting dielectric layer is desirable so as to permit the dielectric to be partially etched away to form a corrugated surface. It would be apparent to one of skill in the art how to control the thickness of a dielectric layer during deposition onto a given substrate. By way of example only, a suitable process for depositing the insulating dielectric layer 104b on the conductive layer 104a includes, but is not limited to, chemical vapor deposition (CVD).

Graphene is a material that consists of one atom thick sheets of carbon. According to an exemplary embodiment, graphene layer 102 actually includes from 1 (i.e., a graphene monolayer) up to a stack of about 5 graphene sheets, and ranges therebetween. By way of example only, graphene layer 102 may be deposited (or grown) on the substrate 104 using any suitable deposition process including, but not limited to, mechanical exfoliation, epitaxial growth, a transfer process and CVD. While exfoliation is ideal for obtaining high quality (i.e., low amount of structural defects), there are tradeoffs. For instance, the dimensions (size, thickness, etc.) of the sample are hard to control with exfoliation. Thus, processes such as CVD of graphene can be a viable alternative. A CVD process for graphene deposition is described, for example, in Mattevi et al., "A review of chemical vapour deposition of graphene on copper," J. Mater. Chem., 2011, 21, 3324-3334 (first published November 2010) (hereinafter "Mattevi"), the contents of which are incorporated by reference as if fully set forth herein. Alternatively, graphene sheets grown on another substrate (e.g., by CVD on a copper substrate—see Mattevi) can be subsequently transferred to the substrate 104. See, for example, Ko et al., "Simple method to transfer graphene from metallic catalytic substrates to flexible surfaces without chemical etching," Journal of Physics: Conference Series, Vol. 433, Issue 1 (April 2013) 012002 (hereinafter "Ko"), the contents of which are incorporated by reference as if fully set forth herein.

Optionally, the graphene may be doped. Doping of the graphene can (optionally) be performed at a number of different points in the process. For instance, the graphene can be doped before, after, or during (i.e., in situ doping) being transferred or deposited onto the substrate. Suitable dopants for the graphene include, but are not limited to, polyethylene imine (PEI) (n-type) and diazonium salts (p-type). See, for example, Farmer et al., "Behavior of a Chemically Doped Graphene Junction," Applied Physics Letters 94, 213106 (May 2009), the contents of which are incorporated by reference as if fully set forth herein. Doping of the graphene modifies the carrier concentration, and hence plasmon resonance, in the graphene. Accordingly, doping may be used instead of, or in addition to, back-gating the sensor. It is notable however that being able to back gate the sensor is advantageous to permit in situ adjustments to be made. Thus a back gate (i.e., conductive layer) is included in each of the embodiments described herein with the understanding that graphene doping alone may be employed (in which case a back gate would not be needed). The effects of back-gating doped graphene to alter the carrier concentration are described in detail below.

As will be described in detail below, in this exemplary embodiment, the graphene 102 is divided into multiple nanoribbons using, for example, a lithography and etching process. The term "nanoribbon" as used herein generally refers to strips of graphene each having a width w of from about 50 nm to about 5 micrometers, and ranges therebetween. See below. Since the graphene nanoribbons are to be patterned from graphene layer 102, each of the nanoribbons likewise will consist of from about 1 (a monolayer) up to a stack of about 5 sheets of graphene and ranges therebetween. As will be described in detail below, the width of the nanoribbons is one factor (e.g., along with the charge density) that affects, and thus can be used to control, the plasmon resonance. An example showing the effect of varying nanoribbon width is shown illustrated in FIG. 19, described below.

To form the graphene 102 into nanoribbons, an etch mask 202 is first patterned on the graphene 102. See FIG. 2. Specifically, to form the etch mask 202, a resist material is first deposited onto a side of graphene layer 102 opposite the substrate 104. Standard lithography and etching techniques are then employed to pattern the resist material into the etch mask 202. By way of example only, a suitable resist material includes, but is not limited to, polymethyl methacrylate (PMMA). PMMA can be spin-coated onto the graphene layer 102 and patterned, e.g., using e-beam lithography. A pre bake (prior to patterning) of a PMMA resist is preferably employed, e.g., at a temperature of from about 170 degrees Celsius (° C.) to about 190° C. and ranges therebetween, for a duration of from about 1 minute to about 30 minutes and ranges therebetween. Following patterning, an optional postbake and hardening of the PMMA may be conducted, e.g., at a temperature of from about 90° C. to about 110° C. and ranges therebetween, for a duration of from about 1 minute to about 30 minutes and ranges therebetween.

Figure 3:
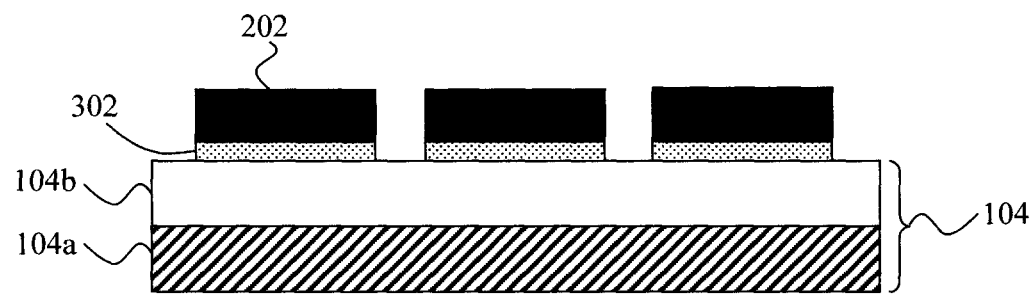
FIG. 3 is a cross-sectional diagram illustrating the etch mask having been used to pattern the graphene layer into the graphene nanoribbons according to an embodiment of the present invention.

Next, as shown illustrated in FIG. 3, the etch mask 202 is used to pattern the graphene layer 202 into multiple graphene nanoribbons 302. According to an exemplary embodiment, this etching step is carried out using a dry etching process, such as an oxygen reactive ion etching (RIE)

process, which is used to etch away the graphene not covered by the etch mask 202 (i.e., the graphene is etched through the etch mask 202).

Following patterning of the nanoribbons 302, the etch mask 202 is removed. See FIG. 4. By way of example only, when the etch mask 202 is formed from PMMA, it can be dissolved in acetone. As highlighted above, the width of the resulting nanoribbons 302 affects, and thus can be used to control, the plasmon resonance. In general, as the dimension (e.g., width w—see below) of the graphene structure decreases the plasmon resonance frequency increases, and vice versa. While there may be different quantitative relations for different structure shapes, this is the general trend. It is also notable that the 'critical dimension' of the graphene with respect to plasmon resonance is the dimension that is parallel to the polarization of the incident light. For example, with nanoribbons, plasmons are excited in graphene when the light polarization is parallel to the width (small dimension) of the nanoribbon. Plasmons are not excited when the light polarization is parallel to the length (large dimension) of the nanoribbon.

Figure 4:
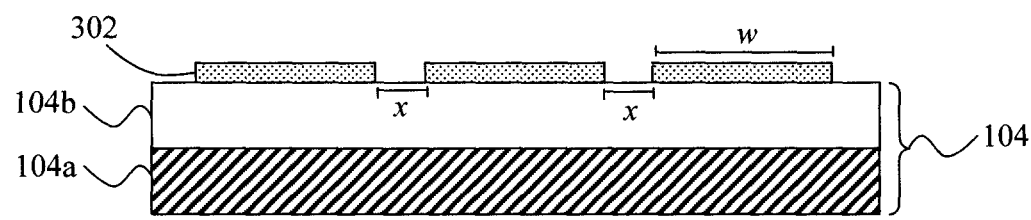
FIG. 4 is a cross-sectional diagram illustrating the etch mask having been removed following patterning of the nanoribbons according to an embodiment of the present invention.

By way of example only, each of the nanoribbons 302 patterned in this step has a width w (see FIG. 4) of from about 50 nm to about 5 micrometers, and ranges therebetween, and consists of from 1 (a monolayer) to a stack of up to about 5 sheets of graphene and ranges therebetween. As shown in FIG. 4, the nanoribbons 302 patterned in this manner form multiple, evenly spaced strips (each having a width w) on the surface of the insulating dielectric layer 104b. This periodic (i.e., occurring at regular intervals), repeating pattern of nanoribbon strips will permit coupling of incident light to the plasmon resonance in the graphene. According to an exemplary embodiment, the strips (i.e., nanoribbons 302) are separated from each other by a distance x. Specifically, each strip (i.e., nanoribbon 302) is separated from an adjacent nanoribbon(s) 302 to either side by a distance x, wherein x is from about 5 nm to about 50 micrometers (μm) and ranges therebetween.

During operation of the sensor, the patterned graphene (i.e., nanoribbons 302) will permit coupling of incident light with the graphene plasmons. By comparison, in the case of the bulk graphene-based sensors described below, this coupling occurs via the formation of regions of different dielectric permittivity. In either the case of patterned graphene nanoribbons or bulk graphene over regions of different dielectric permittivity, coupling of incident light with the graphene plasmons occurs as a result of a general grating effect that is ubiquitous in plasmonics. In general, the grating (periodic regions of differing permittivity) is a coupler, matching the surface-parallel component of the light wavevector with the plasmon wavevector. The amount of matching depends on the period of the grating and wavelength of the light. The underlying plasmon excitation mechanism is the same in both cases since in both cases there is a grating, i.e., regions of differing periodic permittivity.

Figure 5:
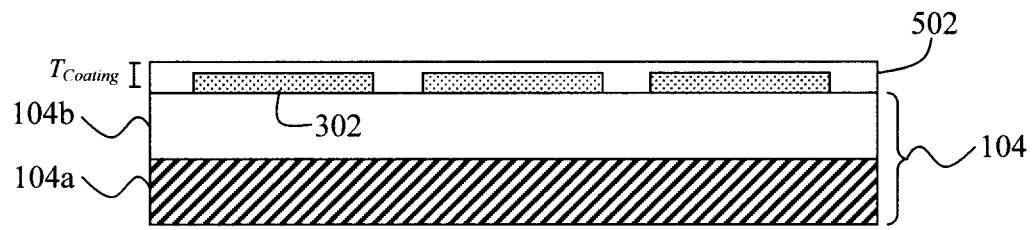
FIG. 5 is a cross-sectional diagram illustrating an optional coating having been deposited onto the substrate covering and protecting the graphene nanoribbons according to an embodiment of the present invention.

Finally, as shown in FIG. 5 an optional coating 502 can be deposited onto the substrate 104 covering the nanoribbons 302 to protect the graphene nanoribbons 302 during use of the device. According to an exemplary embodiment, this optional protective coating 502 is formed from a transparent dielectric material, such as silicon dioxide. When present, the optional protective coating is thin enough to allow the plasmon field to extend through it, maintaining plasmon-induced signal modification. By way of example only, the protective coating has a thickness $T_{Coating}$ of from about 1 nm to about 5 nm and ranges therebetween, e.g., wherein $T_{Coating}$ is measured at a thickest part of the coating 502. See FIG. 5.

As will be described in detail below, when the present graphene-based SPR sensors are used to analyze a sample, the sample is deposited onto (the graphene side of) the sensor and light may be passed (from a light source proximal to the graphene side of the sensor) through both the sample and the sensor and is picked up by a detector (proximal to the substrate side of the sensor). In that case, all components of the sensor should be substantially transparent to the frequency range of the light being used. The above-described materials meet those criteria. While the insulating dielectrics may absorb some small amount of light in certain spectral ranges, this will not have an impact on the readings. More at issue is the back gate material (e.g., conductive layer 104a). Normal metals might not work for a transmission measurement (but could work for a reflection measurement). For transmission, the back gate material can be intrinsic silicon. Intrinsic silicon is transparent in the correct spectral range and can also be used as an electrostatic gate electrode.

The present graphene-based SPR sensors may also be produced using bulk graphene. The use of bulk graphene eliminates the (above-described) steps needed to pattern the graphene nanoribbons, thus simplifying the process. It is notable that while a simplified process is easier to implement and lowers overall production costs, one tradeoff of bulk graphene versus nanoribbons is a loss in the ability to tune the plasmon resonance by graphene patterning (i.e., the width of the nanoribbons can be tailored to tune the plasmon resonance—see above).

A first exemplary process for forming the present SPR sensors using bulk graphene is now provided by way of reference to FIGS. 6-11. As will be described in detail below, the bulk graphene-based embodiments, employ patterning a surface of the substrate onto which the graphene is deposited. The patterned substrate surface provides the sensor with periodic regions of differing (light) permittivity provided by portions of the insulating dielectric substrate and a second material, respectively. In the exemplary embodiment illustrated in FIGS. 6-11, the second material is air, and in another bulk graphene-based embodiment illustrated in FIGS. 12-16, the second material is a dielectric with a different permittivity from the substrate dielectric.

Figure 6:
FIG. 6 is a cross-sectional diagram illustrating a starting structure for an alternative process for forming a graphene-based SPR sensor using bulk graphene, the structure including a dielectric layer opposite a conductive layer according to an embodiment of the present invention.

Referring now to FIG. 6, an exemplary process for forming the present SPR sensors using bulk graphene begins with a substrate 602 which includes a (electrically) conductive layer 602a (which will serve as a back gate of the sensor—see below) and an insulating dielectric layer 602b deposited on the conductive layer 602a. By comparison with the embodiment illustrated in FIGS. 1-5, described above, the insulating dielectric layer 602b initially needs to be thicker to permit further processing of the layer, e.g., so as to form a corrugated surface. See below. Thus, according to an exemplary embodiment, the insulating dielectric layer 602b has a thickness $T_{Dielectric2}$ of from about 4 nm to about 300 nm and ranges therebetween. See FIG. 6. It would be apparent to one of skill in the art how to control the thickness of a dielectric layer during deposition onto a given substrate. By way of example only, a suitable process for depositing the insulating dielectric layer 602b on the conductive layer 602a includes, but is not limited to, CVD.

As above, a suitable (electrically conductive) material for forming conductive layer 602a includes, but is not limited to, intrinsic silicon. Embodiments of the present techniques involve analyzing a sample by passing light through the sample and the sensor (a transmission measurement). In that case, intrinsic silicon is ideal since it is transparent in the correct spectral range and can also be used as an electrostatic gate electrode. Alternatively, conventional gate metals might be employed. For example, one or more of tantalum, titanium, platinum and/or tungsten may be used in forming the conductive layer 602a. However, since these gate metals are not transparent to light, configurations of the present sensors employing a metal back gate would need to be read via a reflection measurement. Any insulating dielectric would be a suitable material for forming insulating dielectric layer 602b. Examples include, but are not limited to, gate dielectrics such as silicon dioxide, aluminum oxide, and high-κ dielectrics such as hafnium oxide or lanthanum oxide.

Next, the insulating dielectric layer 602b of substrate 602 is patterned to form a corrugated surface. Specifically, portions of the insulating dielectric layer 602b will be etched away resulting in the formation of a grated surface of the insulating dielectric layer 602b (opposite the conductive layer 602a) onto which the bulk graphene is deposited.

Figure 7:
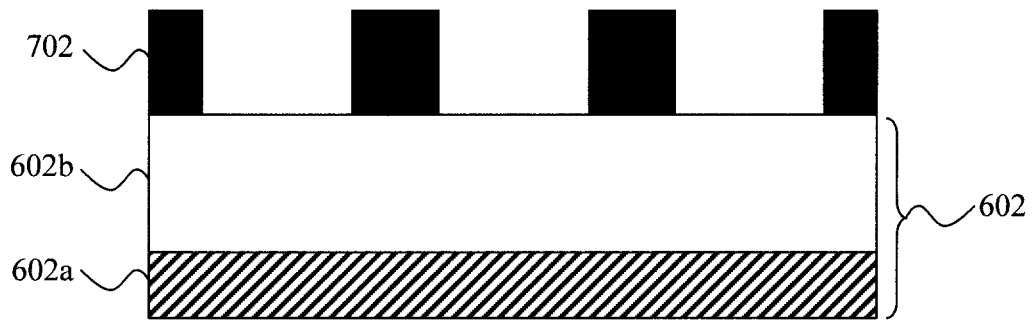
FIG. 7 is a cross-sectional diagram which, following from FIG. 6, illustrates an etch mask having been formed on the dielectric layer according to an embodiment of the present invention.

As shown in FIG. 7, the process of patterning of the insulating dielectric layer 602b begins with the formation of an etch mask 702 on the insulating dielectric layer 602b. Specifically, to form the etch mask 702, a resist material is first deposited onto a side of the insulating dielectric layer 602b opposite the conductive layer 602a. Standard lithography and etching techniques are then employed to pattern the resist material into the etch mask 702. By way of example only, a suitable resist material includes, but is not limited to, PMMA. As described in detail above, PMMA can be spin-coated onto the substrate and patterned, e.g., using e-beam lithography. As described above, a pre bake and an optional postbake of the PMMA resist can be performed. Exemplary parameters (i.e., temperature and duration) of these baking steps were provided above.

Figure 8:
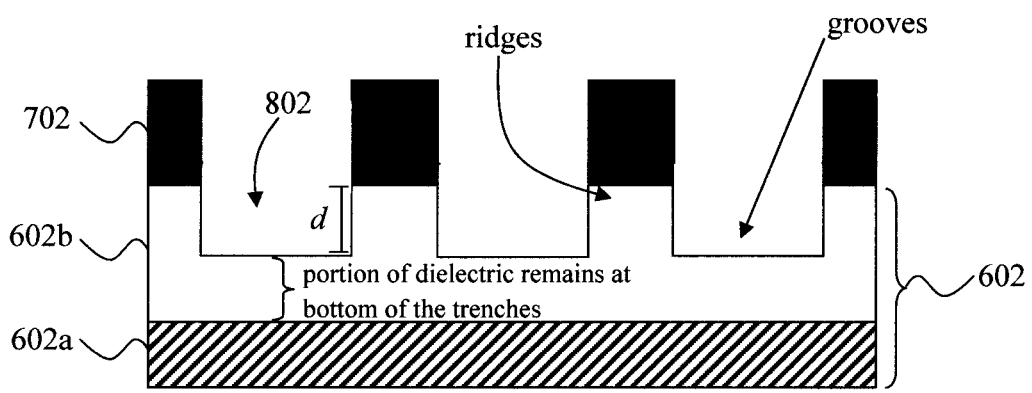
FIG. 8 is a cross-sectional diagram which, following from FIG. 7, illustrates the etch mask having been used to pattern the insulating dielectric layer according to an embodiment of the present invention.

The etch mask 702 is then used to pattern the insulating dielectric layer 602b. See FIG. 8. Specifically, the etch mask 702 is used to pattern trenches at regular intervals in the surface of insulating dielectric layer 602b to transform the surface of insulating dielectric layer 602b into a grated or corrugated surface having a series of grooves (formed by the trenches 802) and ridges (formed by the portions of the insulating dielectric layer 602b remaining in between the trenches 802). See FIG. 8. As shown in FIG. 8 it is desirable to time the etch so as not to etch completely through the insulating dielectric layer 602b (i.e., following the etch, a portion of the insulating dielectric layer 602b preferably remains at the bottom of each of the trenches 802). Thus the trenches 802 extend only partway through the dielectric layer 602b. By way of example only, a RIE process may be used to remove portions of the insulating dielectric layer 602b not covered by the etch mask 702. The RIE may be endpointed prior to completely etching through the insulating dielectric layer 602b. A reason for leaving a portion of the insulating dielectric layer 602b at the bottom of each of the trenches 802 is to prevent the graphene, which may potentially bend into the trench during operation, from touching the exposed conductive material and "shorting" the device. According to an exemplary embodiment, this portion of the insulating dielectric layer left at the bottom of the trenches has a minimum thickness of about 5 nm, e.g., from about 5 nm to about 20 nm and ranges therebetween. Further, the deeper the trenches 802, the better, because the dielectric mismatch will be enhanced. By way of example only, each of the trenches 802 preferably has a depth d of from about 4 nm to about 300 nm and ranges therebetween.

Figure 9:
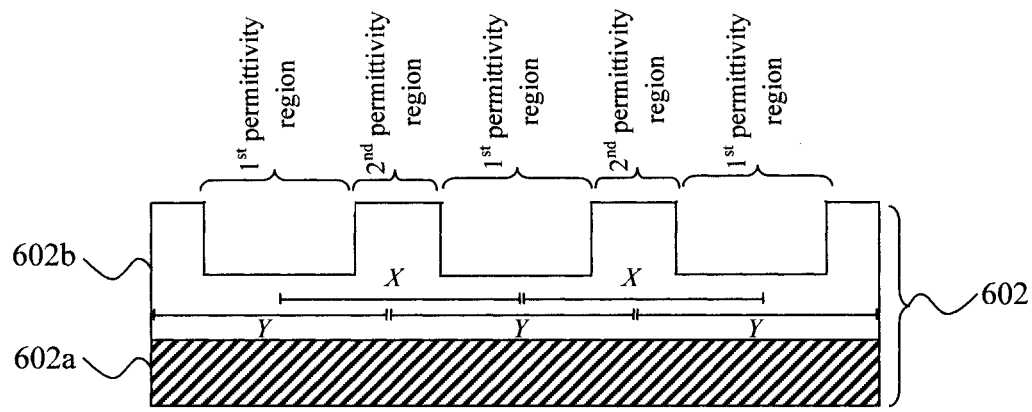
FIG. 9 is a cross-sectional diagram which, following from FIG. 8, illustrates the etch mask having been removed revealing that the patterned insulating dielectric layer has a corrugated surface consisting of ridges and grooves according to an embodiment of the present invention.

The goal here is to produce a dielectric surface (onto which graphene can be deposited) that consists of regions of different (light) permittivity. In this example, the ridges in the insulating dielectric layer 602b surface serve as the first regions, wherein the insulating dielectric layer 602b has a first permittivity to light. The grooves formed by the trenches 802 in the insulating dielectric layer 602b surface serve as the second regions, wherein the air within the trenches 802 has a second permittivity to light. See FIG. 9. This periodic (i.e., occurring at regular intervals), repeating, alternating of regions of differing permittivity will permit coupling of incident light to the plasmon resonance in the graphene. According to an exemplary embodiment, the first regions are separated from each other by a (first) distance X (measured as a distance from a center of one first region to a center of another, adjacent first region) and the second regions are separated from each other by a (second) distance Y (measured as a distance from a center of one second region to a center of another, adjacent second region), wherein X and Y each are from about 5 nm to about 20 nm and ranges therebetween. As also shown in FIG. 9, following patterning of the trenches 802, the etch mask 702 may be removed. By way of example only, when the etch mask 702 is formed from PMMA, it can be dissolved in acetone.

Figure 10:
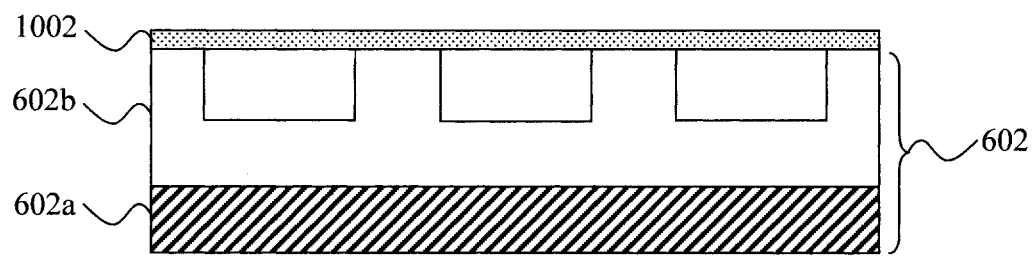
FIG. 10 is a cross-sectional diagram which, following from FIG. 9, illustrates graphene having been deposited onto the substrate according to an embodiment of the present invention.

Following the dielectric etch (and etch mask removal), graphene 1002 is then deposited onto the substrate. See FIG. 10. Specifically, as shown in FIG. 10, the graphene 1002 is deposited onto the now corrugated surface of the insulating dielectric layer 602b (i.e., the side of the insulating dielectric layer 602b opposite the conductive layer 602a). With this configuration, the graphene 1002 will cover both i) the first regions (the ridges in the insulating dielectric layer 602b) having the first permittivity to light and ii) the second regions (the grooves formed by the trenches in the insulating dielectric layer 602b which are filled with air) having the second permittivity to light. Coupling of incident light with graphene plasmons is thus allowed due to the periodic permittivity of the surface. As described above, the periodic grating (either via the patterned graphene nanoribbons or the regions of different dielectric permittivity) allows for matching of the light wavevector and plasmon wavevector, and therefore coupling of the incident light with the plasmon.

As above, the graphene 1002 may be a layer having from 1 (i.e., a graphene monolayer) up to a stack of about 5 graphene sheets, and ranges therebetween. Suitable processes for depositing and/or growing graphene were described above. However, in this case, the desired result is a planar layer of graphene over the ridges and grooves in the surface of the insulating dielectric layer 602b. Thus, a transfer process is preferable, wherein a sheet(s) of the graphene are transferred to the corrugated surface of the insulating dielectric layer 602b over the ridges and grooves. See FIG. 10. By way of example only, graphene sheets grown on another substrate (e.g., by CVD on a copper substrate—see Mattevi) can be subsequently transferred to the (corrugated) surface of the insulating dielectric layer 602b. See, for example, Ko. In this case, the graphene 1002 is not patterned into ribbons, and thus can remain in its as deposited, bulk form.

As above, the graphene may optionally be doped to modify the carrier concentration, and hence plasmon resonance, in the graphene. Suitable dopants include, but are not limited to, PEI (n-type) and diazonium salts (p-type). As described above, while doping may be used instead of back-gating the sensor, having a back gate is advantageous to permit in situ adjustments to be made. Thus it may be desirable to have a back gate in combination with a doped graphene layer. The effects of backgating doped graphene to alter the carrier concentration are described in detail below.

Figure 11:
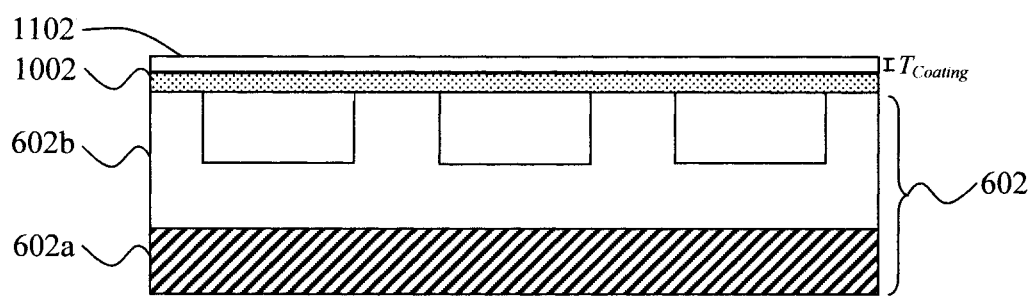
FIG. 11 is a cross-sectional diagram which, following from FIG. 10, illustrates an optional coating having been deposited onto the sensor to cover and protect the graphene according to an embodiment of the present invention.

Finally, as shown in FIG. 11 an optional coating 1102 can be deposited onto the sensor covering the graphene layer 1002 to protect the graphene during use of the device. As provided above, this optional protective coating 1102 can be formed from a transparent dielectric material, such as silicon dioxide, and should be thin enough to allow the plasmon field to extend through it, maintaining plasmon-induced signal modification. By way of example only, the protective coating has a thickness $T_{Coating}$ of from about 1 nm to about 5 nm and ranges therebetween. See FIG. 11.

While providing periodic regions of different permittivity using air (present in the trenches of the corrugated surface) as one of the materials, there is a chance that electrostatic forces might cause the graphene to bend into the grooves formed by the trenches. To prevent this distortion of the graphene from occurring, it is also possible to employ a material (other than air) in the trenches having a different permittivity (to light). In the example illustrated in FIGS. 12-16, this material is a different dielectric material from that used in the substrate which has a different permittivity to light. Like the embodiment illustrated in FIGS. 6-11, this process also employs bulk graphene.

As with the other bulk graphene-based example illustrated in FIGS. 6-11, this exemplary embodiment also involves patterning the substrate dielectric to form a corrugated surface thereon. Therefore, the first few steps of the two bulk graphene-based process flows are the same. Specifically, each begins with a thick insulating dielectric layer 602b on a conductive layer 602a. See FIG. 6, described above. An etch mask 702 is then formed on a side of the insulating dielectric layer 602b opposite the conductive layer 602a. As described above, the etch mask 702, e.g., via a RIE process, will be used to pattern the insulating dielectric layer 602b into a corrugated layer including ridges and grooves.

Figure 12:
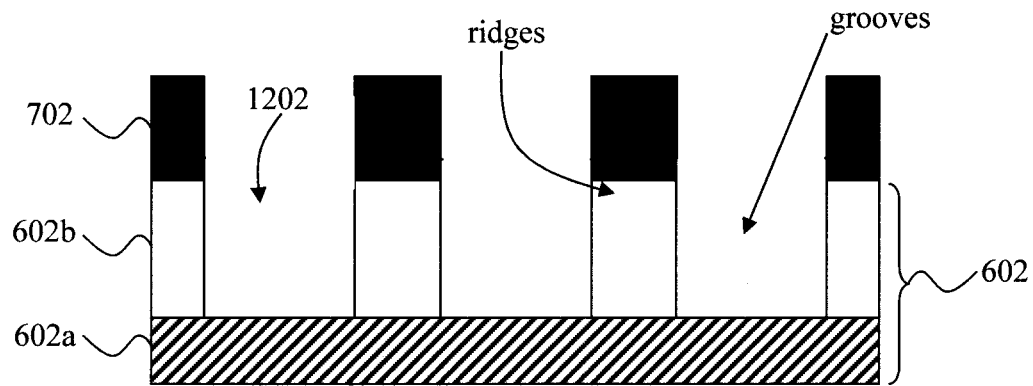
FIG. 12 is a cross-sectional diagram which, following from FIG. 7, illustrates in an alternative bulk graphene-based embodiment the etch mask having been used to pattern trenches in the insulating dielectric layer that extend down to the surface of the conductive layer according to an embodiment of the present invention.
Figure 13:
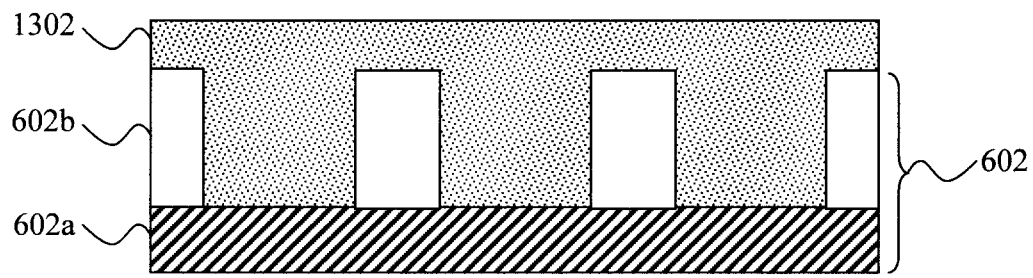
FIG. 13 is a cross-sectional diagram which, following from FIG. 12, illustrates a second (different permittivity) material having been deposited onto the substrate, overfilling each of the trenches according to an embodiment of the present invention.

It is at this point in the process flow where the two techniques differ. Thus, following from FIG. 7, FIG. 12 illustrates how in this case an etch is used to remove portions of the insulating dielectric layer 602b not covered by etch mask 702 down to the conductive layer 602a, resulting in the formation of trenches 1202 that extend down to the surface of the conductive layer 602a. See FIG. 12. Specifically, since the trenches 1202 will be filled (e.g., with a different dielectric material), then it is not necessary that any of the insulating dielectric layer 602b material remain in the trenches (compare, for example, FIG. 12 with FIG. 8—described above).

As described above, the goal of etching the insulating dielectric layer 602b is to pattern trenches 1202 at regular intervals in the insulating dielectric layer 602b to transform the insulating dielectric layer 602b into a grated or corrugated layer having a series of grooves (formed by the trenches 1202) and ridges (formed by the portions of the insulating dielectric layer 602b remaining in between the trenches 1202). See FIG. 12. In this case, however, the trenches 1202 preferably extend completely through the insulating dielectric layer 602b down to the surface of the conductive layer 602a. According to an exemplary embodiment, a RIE process is used to pattern the insulating dielectric layer 602b through the etch mask 702. In this case, the conductive layer 602a can serve as an etch stop for the RIE. Following the trench etch, the etch mask 702 can be removed. By way of example only, when the etch mask 702 is formed from PMMA, it can be dissolved in acetone.

The goal here is to produce a dielectric surface (onto which graphene can be deposited) that consists of regions of different (light) permittivity. In this example, the ridges in the insulating dielectric layer 602b surface serve as the first regions, wherein the insulating dielectric layer 602b has a first permittivity to light. A second material which will be filled into the grooves formed by the trenches 1202 in the insulating dielectric layer 602b surface will serve as the second regions, wherein the second material has a second permittivity to light. See FIG. 14, described below.

Specifically, after the etch mask 702 has been removed, the process for filling the trenches 1202 with a second (different permittivity) material begins by blanket depositing the second material 1302 onto the substrate, overfilling each of the trenches 1202. See FIG. 13. By way of example only, the insulating dielectric layer 602b can be silicon dioxide (see above), and the second material 1302 can be aluminum oxide or hafnium oxide, or vice versa. Strictly speaking, all materials have different permittivities because of their different elemental compositions. Thus using two different dielectric materials for dielectric layer 602b and material 1302 would result in different permittivities. However, it is desirable here to have the highest permittivity mismatch possible. That will generate the strongest plasmon excitation. Therefore, the combination of a high-κ material like hafnium oxide (κ=20) and silicon dioxide (κ=4) would be good. Even better is a vacuum (κ=1) in combination with a high-κ dielectric, which can be realized in the embodiment where the trenches are left empty and covered over with bulk graphene. See FIG. 10, described above.

In order to provide a flat surface onto which the graphene can be deposited, the second material 1302 is then polished down to the surface of the insulating dielectric layer 602b. As a result, a surface of the second material 1302 will be coplanar with a top surface of the ridges in the insulating dielectric layer 602b. See FIG. 14. According to an exemplary embodiment, the second material 1302 is polished using chemical mechanical polishing (CMP). Depending on the selectivity of the CMP process, this polishing step will also serve to planarize the tops of the ridges, additionally insuring that a flat surface is provided for graphene deposition.

Figure 14:
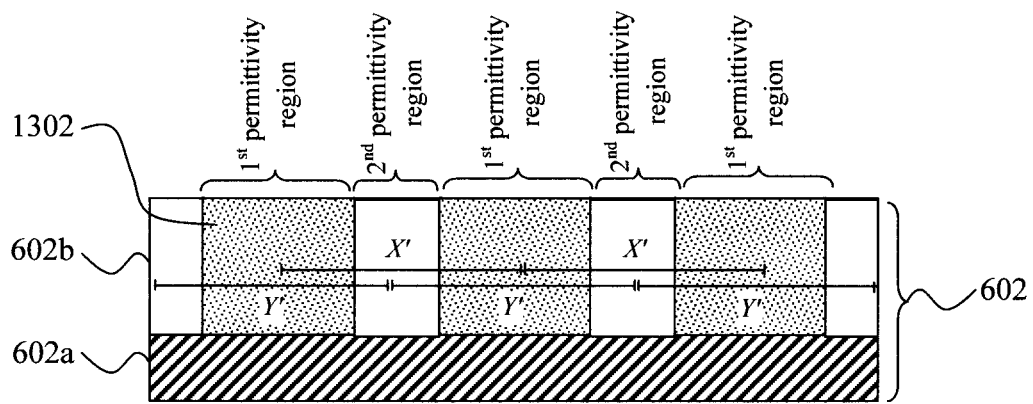
FIG. 14 is a cross-sectional diagram which, following from FIG. 13, illustrates the second material having been polished down to the surface of the insulating dielectric layer according to an embodiment of the present invention.

As shown in FIG. 14, the result is the substrate having periodic regions of different permittivity wherein the first regions (formed from the ridges in the insulating dielectric layer 602b) have a first permittivity to light, and the second regions (formed from the second material 1302 filled in the trenches) have a second permittivity to light. This periodic (i.e., occurring at regular intervals), repeating, alternating of regions of differing permittivity will permit coupling of incident light to the plasmon resonance in the graphene. According to an exemplary embodiment, the first regions are separated from each other by a (first) distance X' (measured as a distance from a center of one first region to a center of another, adjacent first region) and the second regions are separated from each other by a (second) distance Y' (measured as a distance from a center of one second region to a center of another, adjacent second region), wherein X' and Y' each are from about 5 nm to about 20 nm and ranges therebetween.

Figure 15:
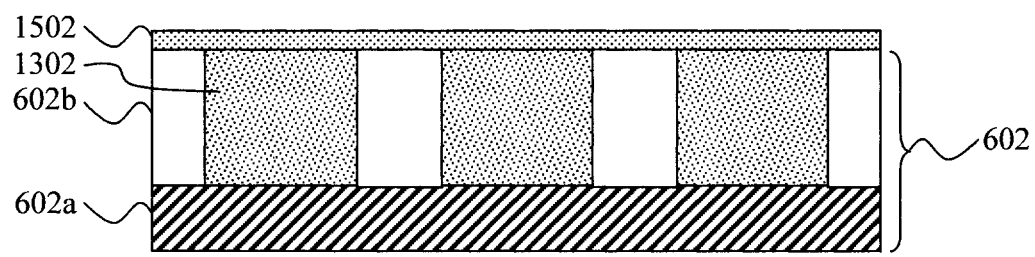
FIG. 15 is a cross-sectional diagram which, following from FIG. 14, illustrates graphene having been deposited onto the substrate according to an embodiment of the present invention.

Graphene 1502 is then deposited onto the substrate. See FIG. 15. Specifically, as shown in FIG. 15, the graphene 1502 is deposited onto the surface of the substrate opposite the conductive layer 602a now having periodic regions of different permittivity from the alternating materials of different permittivity on that surface (e.g., the alternating ridges in insulating dielectric layer 602b and the second material 1302 in the trenches therebetween). Thus, with this configuration, the graphene 1502 will cover both i) the first regions (the ridges in the insulating dielectric layer 602*b*) having the first permittivity to light and ii) the second regions (the grooves formed by the trenches in the insulating dielectric layer 602*b* which are filled with the second material 1302) having the second permittivity to light. Coupling of incident light with graphene plasmons is thus allowed due to the periodic permittivity of the surface. As described above, the periodic grating (either via the patterned graphene nanoribbons or the regions of different dielectric permittivity) allows for matching of the light wavevector and plasmon wavevector, and therefore coupling of the incident light with the plasmon.

As above, the graphene 1502 may be a layer having from 1 (i.e., a graphene monolayer) up to a stack of about 5 graphene sheets, and ranges therebetween. Suitable processes for depositing and/or growing graphene were described above. By comparison with the example provided in FIGS. 6-11 above wherein the graphene is deposited over the empty grooves (and ridges), here the grooves are filled with a second material (other than air). Thus, a planar surface is present onto which the graphene can be deposited. Accordingly, any of the above-described exemplary processes for depositing (or growing) graphene on a surface which include, but are not limited to, mechanical exfoliation, epitaxial growth, a transfer process and CVD, may be employed. In this case, the graphene 1502 is not patterned into ribbons, and thus can remain in its as deposited, bulk form.

Figure 16:
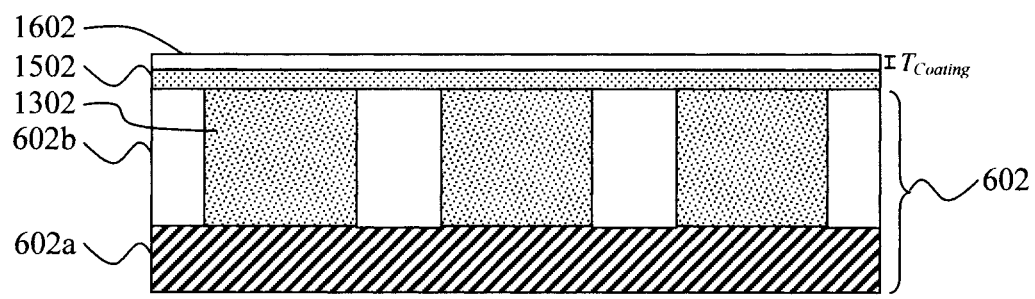
FIG. 16 is a cross-sectional diagram which, following from FIG. 15, illustrates an optional coating having been deposited onto the sensor to cover and protect the graphene according to an embodiment of the present invention.

Finally, as shown in FIG. 16 an optional coating 1602 can be deposited onto the sensor covering the graphene layer 1502 to protect the graphene during use of the device. As provided above, this optional protective coating 1602 can be formed from a transparent dielectric material, such as silicon dioxide, and should be thin enough to allow the plasmon field to extend through it, maintaining plasmon-induced signal modification. By way of example only, the protective coating has a thickness $T_{Coating}$ of from about 1 nm to about 5 nm and ranges therebetween. See FIG. 16.

Figure 17:
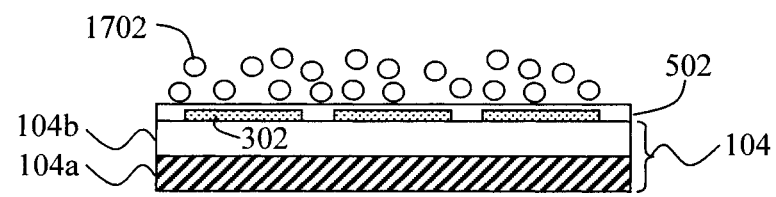
FIG. 17 is a cross-sectional diagram illustrating a sample having been deposited onto the present SPR sensor according to an embodiment of the present invention.
Figure 18:
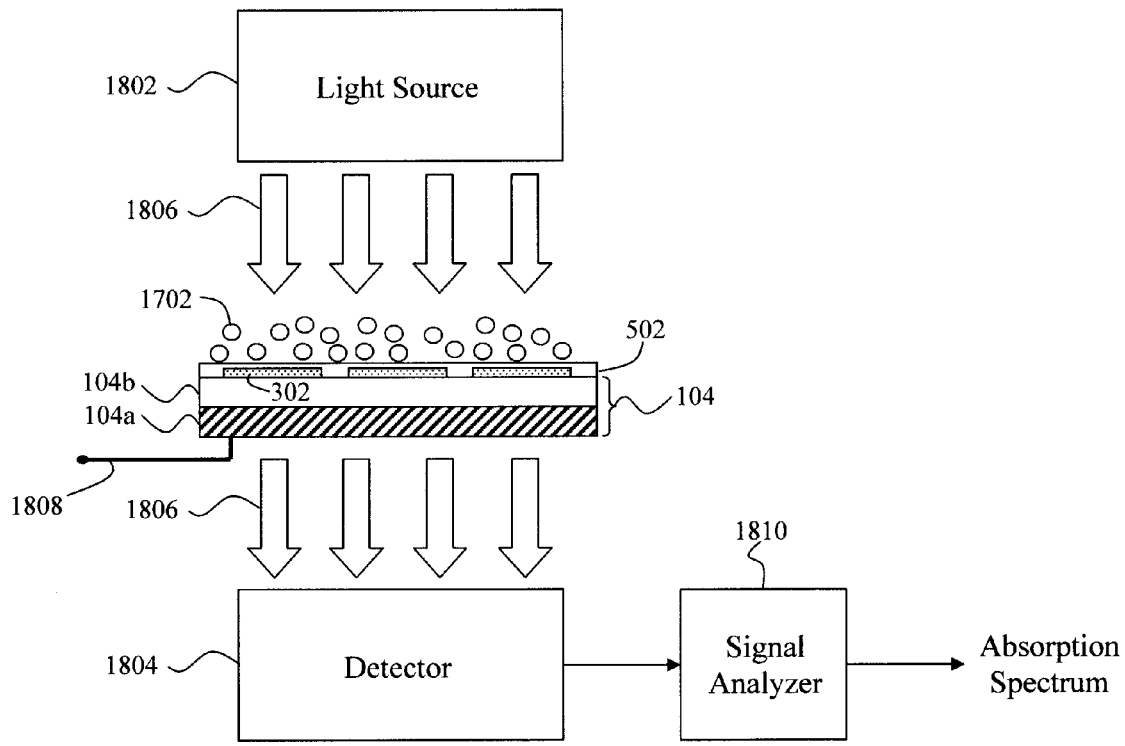
FIG. 18 is a diagram which, following from FIG. 17, illustrates the present SPR sensor being used to analyze the sample according to an embodiment of the present invention.

Exemplary methodologies for using the present graphene-based SPR sensors for analyzing a sample are now described by way of reference to FIGS. 17-18 (transmission measurement) and 20 (reflection measurement). By way of example only, the graphene nanoribbon configuration of the present SPR sensor (of FIGS. 1-5) will be used in the figures to illustrate the implementation process. However, the same process is performed in the same manner with any of the SPR sensor configurations provided herein.

In general, the process will involve applying a sample to the surface of the present SPR sensor, which is subsequently illuminated with a certain spectral range of light. The plasmons in graphene excited by this light interact with the vibrational dipole moments in the sample in such a way as to modulate (change) the output signal of the light transmitted through the sensor. This modulation can be constructive or destructive, is seen in the absorption spectrum of the outgoing light signal, and allows for sensitive identification of molecular compounds associated with chemical and/or biological species.

The details of the process are now provided. As shown in FIG. 17, the first step is to deposit a sample 1702 onto the present SPR sensor. The sensor shown in FIG. 17 has the optional protective coating (i.e., in this case coating 502) in place to protect the graphene during operation of the device. Specifically, as shown in FIG. 17, the sample is deposited onto the graphene (i.e., in this case onto the nanoribbons 302)—or alternatively onto the (optional) protective coating covering the graphene.

In one exemplary embodiment, the sample 1702 is a chemical and/or biological material of interest. For instance, the present sensors may be used to analyze biological samples including samples containing genetic materials (such as DNA or RNA), proteins, enzymes, cell and tissue samples, etc. Chemical sensing and analysis using the present sensors has a broad applicability to a wide variety of fields such as chemical compound and product testing, food analysis, drug analysis, etc. Advantageously, the present SPR sensors can be used to analyze samples for which conventional analytics, such as IR spectroscopy would not be able to detect because the sample is too small.

Generally, the analysis process using the present SPR sensors involves using incident light (provided by a light source) to cause excitation of plasmons in the graphene. Interactions between the particular sample 1702 and the graphene will affect the surface plasmon resonance of the graphene. As a point of reference, a baseline spectrum is preferably acquired without the graphene and sample (substrate). A spectrum with the graphene and sample is then acquired. The final spectrum data can then be given as a ratio between the sample+graphene+substrate spectrum and the substrate spectrum.

With that overall concept in mind, the next step is to provide a light source 1802 proximal to one side of the SPR sensor and the sample 1702 and a detector 1804 proximal to an opposite side of the SPR sensor, such that light 1806 produced by the light source 1802 can pass through the SPR sensor and the sample 1702 to the detector 1804. See FIG. 18. Graphene is transparent to light, as are the conductive layer 104*a* and the insulating dielectric layer 104*b* configured as described above. Thus, the light from the light source 1802 may easily pass through the sensor to the detector 1804. This configuration (i.e., light source and detector on opposite sides of the sensor) assumes that the sensor uses light transparent materials. As described above, the back gate material can be intrinsic silicon which is transparent to light and can serve as an electrostatic gate electrode. Transmission measurements through the sensor may then be made.

On the other hand, if the gate electrode material used is a metal, then transmission measurements are not possible since metals are not transparent to light. In that case, reflection measurements can be made where the light source and the detector are located on the same side of the sensor proximal to the graphene. Incident light from the light source can be reflected off of the surface of the sensor at an angle and captured by the detector. This alternative configuration is shown illustrated in FIG. 20, described below.

One advantage of the present techniques is that surface plasmon resonance of the graphene is tunable by way of the patterning of the graphene nanoribbons (as described above), and also by way of the charge density of the graphene. As such, the charge carrier concentration in graphene is localized in such a way as to promote plasmon excitation. By way of example only, as shown in FIG. 18, the charge density of the graphene can be modulated using the field effect, e.g., by applying a gate voltage 1808 to the conductive layer 104*a* (which in this case serves as a back gate electrode) to modulate the charge density of the graphene. By modulating the charge density in the graphene, the plasmon resonance of the graphene can be shifted. For example, if a sample of interest has an intrinsic internal vibration at frequency A, but the graphene plasmon resonates at frequency B, then the back gate can be used to change the charge density in the graphene and shift the plasmon resonance to overlap with frequency A. For p-doped (or n-doped) graphene, a more negative (or positive) gate bias will induce more charge in the graphene, causing the plasmon resonance to shift to a higher frequency. The more free charge in the graphene, the higher the plasmon frequency (for a constant nanoribbon width).

Another advantage of the present techniques is that prisms are not needed to guide the incident light to the sensors. Specifically, in conventional designs, the angle of the incident light is important to couple the incident light to the resonance of the plasmon material (commonly gold—see above). Without the correct angle, the desired surface plasmon resonance is not produced. Prisms are typically used to direct light at the proper angle to the sensor. While prisms are generally suited in that regard, they must be precisely implemented, which adds to device complexity and to overall production costs. By comparison, with the present SPR sensors, the angle of the incident light is not a factor, since coupling to the graphene can occur with the light source 1802 at any position above the graphene surface of the device. Preferably, as shown in FIG. 18, the light source 1802 and the detector 1804 are positioned in line with one another (based on the path of the light 1806) with the SPR sensor centrally located therebetween.

Light 1806, generated by the light source, is then passed through the sample 1702 and the SPR sensor. See FIG. 18. As described above, the incident light 1806 on the sensor induces a plasmon resonance in the graphene which is affected by the interaction of the sample 1802 and the graphene. As a result, an intensity of the light 1806 exiting the sensor (and which is picked up by the detector 1804) is altered, e.g., as compared to the light 1806 exiting the sensor when no sample is present.

According to an exemplary embodiment, a Fourier transform infrared spectroscopy setup (FTIR) is employed in conjunction with the present SPR sensor wherein a broadband lamp is used as the light source 1802 in a Michelson interferometer with a movable mirror. Light from the interferometer passes through the sample 1702 and the sensor to an infrared detector (e.g., detector 1804), where the light signal is converted to an electrical signal.

As shown in FIG. 18, a signal analyzer 1810 is used to analyze the electrical signal from the detector 1804. As known in the art, a signal analyzer is a device used to extract information from an electrical signal. In this case, the data output from the signal analyzer is an absorption spectrum. See FIG. 18. Suitable lightwave signal analyzers are commercially available, for example, from Agilent Technologies, Santa Clara, Calif. As highlighted above, the plasmon field generated in the present SPR sensor interacts with dipole fields produced by molecular vibrations in the chemical/biological material (i.e., sample 1702) of interest. This interaction results in an absorption signal modification that manifests itself as either an enhancement or reduction of the signal, and this change in the signal allows for more sensitive detection of these molecular species. Specifically, graphene plasmons and vibrational modes in the sample can interact either constructively or destructively with one another, giving either an increase or decrease in the light absorption signal (the IR absorption spectrum). By gating the sensor, as described above, the plasmon resonance frequency in the graphene can be tuned for better coupling with the test species.

The analysis performed as illustrated in FIGS. 17 and 18 on the sample 1702 can be used, for example, to analyze the molecular properties of the sample such as to detect the existence of a molecule in the sample and also for molecular identification. It serves as a signal enhancement platform for the infrared spectroscopy (e.g., FTIR). Thus, any sample analysis performed using IR spectroscopy can be performed in conjunction with the present techniques, however with a finer granularity and precision due to the increased sensitivity afforded by the present graphene-based SPR sensor.

Figure 19:
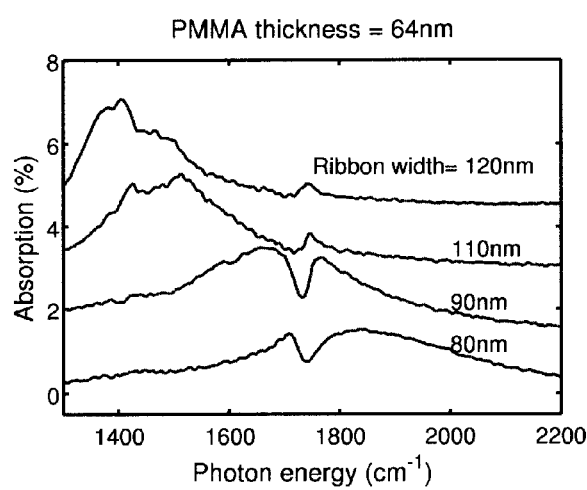
FIG. 19 is a graph illustrating an effect graphene nanoribbons width has on plasma resonance according to an embodiment of the present invention.

As described above, when patterned graphene nanoribbons are used in the present SPR sensors, the width of the nanoribbons is one factor that affects, and thus can be used to control, the plasma resonance. FIG. 19 is a diagram illustrating this effect in an exemplary case where the analyte is a sample of PMMA. In FIG. 19, photon energy is plotted on the x-axis and absorption is plotted on the y-axis. As shown in FIG. 19, the absorption spectrum shifts proportionally with the width of the nanoribbons (labeled "Ribbon width").

Figure 20:
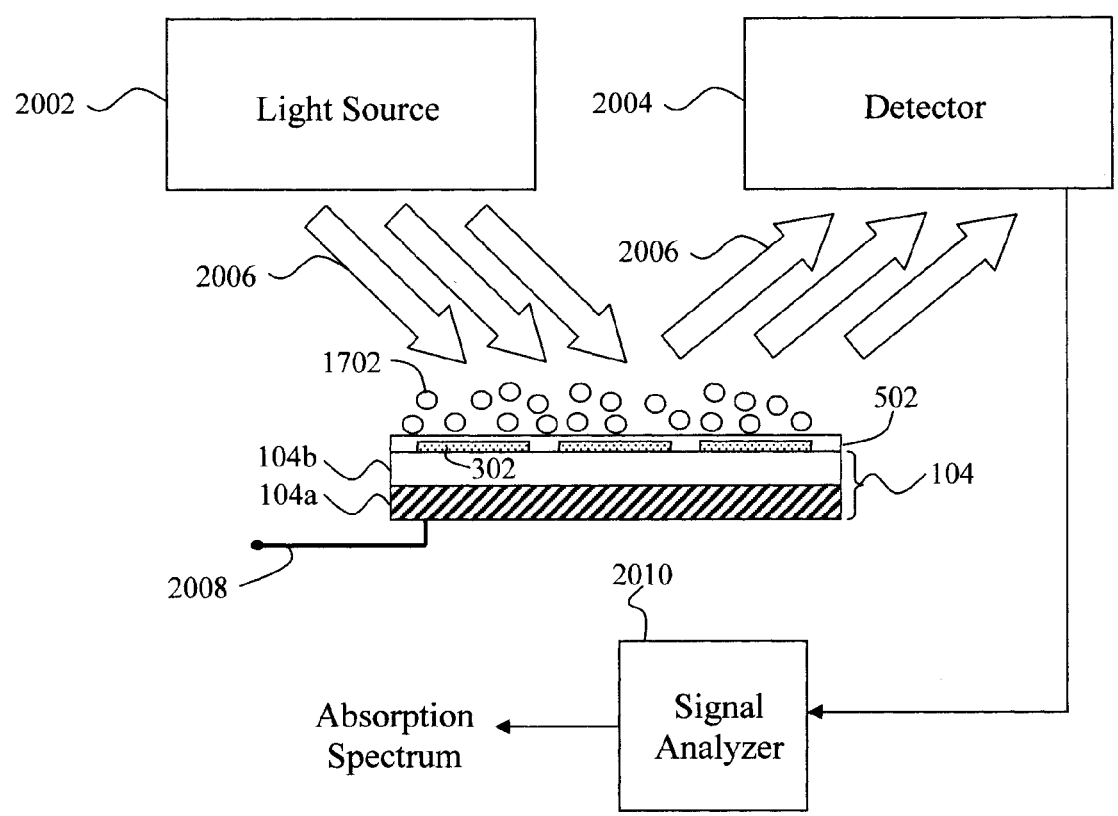
FIG. 20 is a diagram which, following from FIG. 17, illustrates an alternative (reflection measurement-based) use of the present SPR sensor to analyze the sample according to an embodiment of the present invention.

As described above, transmission measurements require that the components of the sensor are transparent to light. Thus when non-transparent materials are used in the sensors (such as metals to form the back gate electrode), then alternate sensing methods are employed, such as reflection measurements. The same analysis process as described in conjunction with the description of FIGS. 17 and 18, above, is employed here, except that both the light source and the detector are located on the same side of the sensor. Thus, following from FIG. 17, as shown in FIG. 20, light 2006, generated by the light source 2002, is reflected off of the (graphene side) surface of the SPR sensor having sample 1702 thereon onto the detector 2004. As described above, the incident light 2006 on the sensor induces a plasmon resonance in the graphene which is affected by the interaction of the sample 1702 and the graphene. As a result, an intensity of the light 2006 reflected off of the sensor (and which is picked up by the detector 2004) is altered, e.g., as compared to the light 2006 reflected from the sensor when no sample is present. As above, the charge density of the graphene can be modulated using the field effect, e.g., by applying a gate voltage 2008 to the conductive layer 104a (which in this case serves as a back gate electrode) to modulate the charge density of the graphene.

A signal analyzer 2010 is used to analyze the electrical signal from the detector 2004. As highlighted above, the plasmon field generated in the present SPR sensor interacts with dipole fields produced by molecular vibrations in the chemical/biological material (i.e., sample 1702) of interest. This interaction results in an absorption signal modification that manifests itself as either an enhancement or reduction of the signal, and this change in the signal allows for more sensitive detection of these molecular species. By gating the sensor, the plasmon resonance frequency in the graphene can be tuned for better coupling with the test species.

Although illustrative embodiments of the present invention have been described herein, it is to be understood that the invention is not limited to those precise embodiments, and that various other changes and modifications may be made by one skilled in the art without departing from the scope of the invention.

What is claimed is:

1. A method of forming a graphene-based SPR sensor, comprising the steps of:
   depositing a dielectric layer on a conductive layer;
   patterning trenches at regular intervals in the dielectric layer to transform the dielectric layer into a corrugated surface having a series of grooves and ridges, wherein the grooves are formed by the trenches and the ridges are formed by the dielectric layer remaining between the trenches; and depositing bulk graphene onto the corrugate surface of the dielectric layer, wherein the corrugated surface of the dielectric layer provides periodic regions of differing permittivity beneath the bulk graphene comprising i) first regions having a first permittivity to light and ii) second regions having a second permittivity to light.

2. The method of claim 1, wherein the trenches are patterned so as to extend only partway through the dielectric layer.

3. The method of claim 2, wherein a portion of the dielectric layer remaining at a bottom of the trenches has a thickness of at least about 5 nanometers.

4. The method of claim 2, wherein a portion of the dielectric layer remaining at a bottom of the trenches has a thickness of from about 5 nanometers to about 20 nanometers and ranges therebetween.

5. The method of claim 1, wherein each of the trenches has a depth of from about 4 nanometers to about 300 nm and ranges therebetween.

6. The method of claim 1, wherein the trenches are patterned so as to extend completely through the dielectric layer, down to a surface of the conductive layer.

7. The method of claim 1, wherein the first regions having the first permittivity to light comprise the ridges formed by the dielectric layer beneath the bulk graphene, and wherein the second regions having the second permittivity to light comprise air in the trenches beneath the bulk graphene.

8. The method of claim 1, wherein the first regions having the first permittivity to light comprise the ridges formed by the dielectric layer beneath the bulk graphene, and wherein the second regions having the second permittivity to light comprise a material in the trenches beneath the bulk graphene having a permittivity to light that is different from the dielectric layer.

9. The method of claim 8, wherein the material having a permittivity to light that is different from the dielectric layer comprises a different dielectric material from the dielectric layer.

10. The method of claim 8, wherein the dielectric layer comprises silicon dioxide, and wherein the material in the trenches comprises a high-κ dielectric.

11. The method of claim 1, wherein the first regions are separated from one another by a first distance that is measured from a center of one of the first regions to a center of an adjacent first region, wherein the second regions are separated from one another by a second distance that is measured from a center of one of the second regions to a center of an adjacent second region, and wherein the first distance and the second distance are each from about 5 nanometers to about 20 nanometers, and ranges therebetween.

12. The method of claim 1, further comprising the step of:
depositing a coating onto the bulk graphene, wherein the coating comprises a transparent dielectric material.

13. The method of claim 12, wherein the coating has a thickness of from about 1 nanometer to about 5 nanometers and ranges therebetween.

14. The method of claim 1, wherein the dielectric layer is deposited onto the conductive layer to a thickness of from about 4 nanometers to about 300 nanometers and ranges therebetween.

15. The method of claim 1, wherein the conductive layer comprises intrinsic silicon.

16. The method of claim 1, wherein the step of patterning the trenches comprises the steps of:
depositing a resist material onto the dielectric layer;
patterning the resist material into an etch mask;
etching the dielectric layer through the etch mask to transform the dielectric layer into the corrugated surface; and
removing the etch mask.

17. The method of claim 16, wherein the resist material comprises polymethyl methacrylate (PMMA), and wherein the resist material is patterned into the etch mask using e-beam lithography.

18. The method of claim 1, wherein the bulk graphene comprises a graphene monolayer.

19. The method of claim 1, wherein the step of depositing the bulk graphene comprises the steps of:
growing the bulk graphene on a substrate; and
transferring the bulk graphene from the substrate to the corrugate surface.

20. The method of claim 1, further comprising the step of:
doping the bulk graphene with an n-type or a p-type dopant.

* * * * *